United States Patent [19]
Renard

[11] 3,960,887
[45] June 1, 1976

[54] CONTINUOUS PROCESS FOR THE PREPARATION OF MALEIMIDES
[75] Inventor: Pierre Renard, Villeurbanne, France
[73] Assignee: Rhone-Poulene, Paris, France
[22] Filed: Nov. 13, 1973
[21] Appl. No.: 415,409

[30] Foreign Application Priority Data
Nov. 16, 1972 France .............................. 72.40700

[52] U.S. Cl. ...................................... 260/326.5 FM
[51] Int. Cl.² ....................................... C07D 207/44
[58] Field of Search ........................... 260/326.5 FM

[56] References Cited
FOREIGN PATENTS OR APPLICATIONS
2,055,969    5/1971    France ............................ 260/326.5

*Primary Examiner*—Joseph A. Narcavage
*Attorney, Agent, or Firm*—Stevens, Davis, Miller & Mosher

[57] ABSTRACT

A continuous process for the preparation of an N-substituted maleimide is provided which comprises
a. reacting, in a first vessel, maleic anhydride and a primary amine in a solvent for the anhydride and amine, under a pressure from 1 to 5 bars and at a temperature from 40° to 130°C,
b. circulating the mixture thus produced through a closed circuit equipped with a condenser, while introuding a dehydrating agent, a tertiary amine and a catalyst into said circuit,
c. continuously removing part of the reaction mixture which is circulating in the circuit, and
d. isolating the maleimide from the mixture thus removed. This process eliminates many of the problems of earlier processes while providing good yields quickly.

11 Claims, 1 Drawing Figure

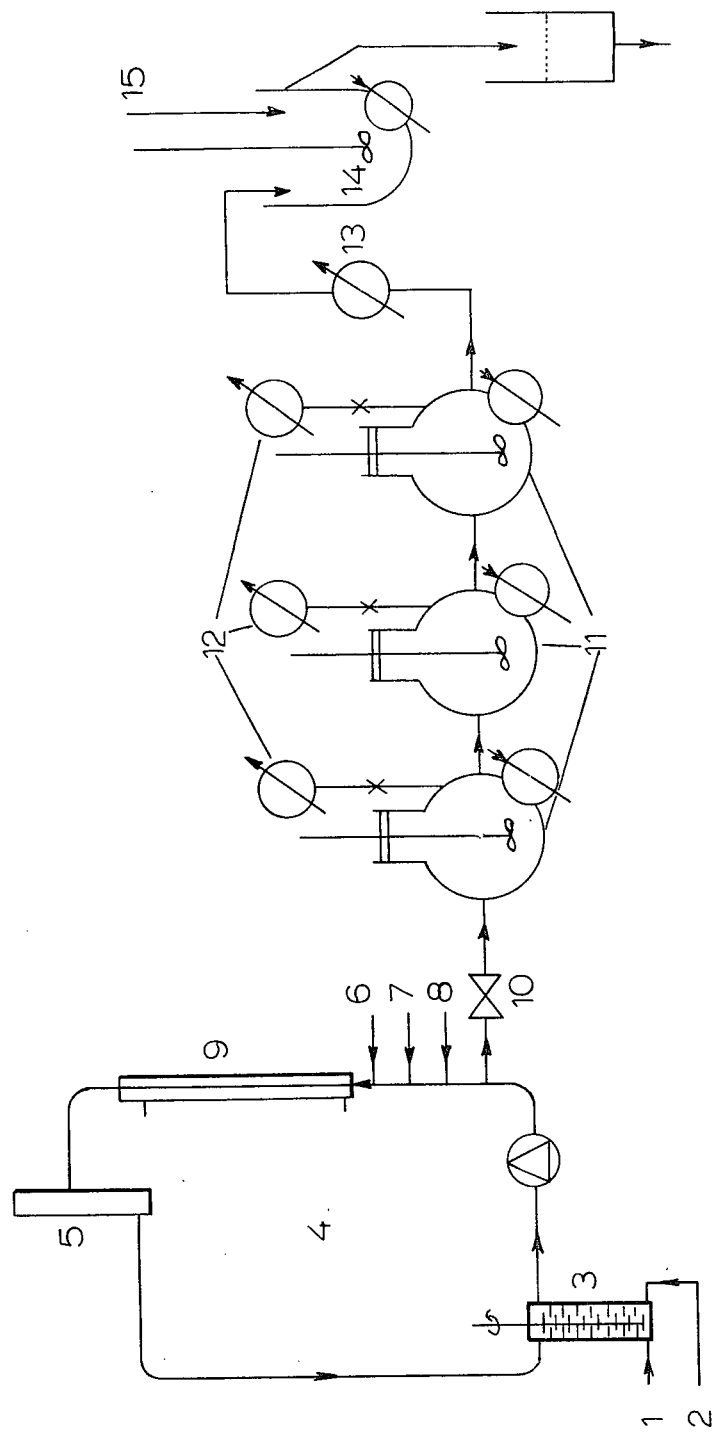

CONTINUOUS PROCESS FOR THE PREPARATION OF MALEIMIDES

The present invention relates to a continuous process for the preparation of maleimides from maleic anhydride and a primary amine.

Various processes enable maleamic acids to be produced from maleic anhydride and a primary amine, see for example, U.S. Pat. Nos. 2,444,536 and 2,723,991 and "Maleic Anhydride Derivatives" by L. A. Flett and W. H. Gardner.

It is known that maleamic acids, which possess a group of the formula

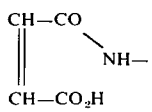

can, under certain circumstances, undergo a cyclising dehydration to form the corresponding maleimide.

Thus, in U.S. Pat. No. 2,444,536, it has been proposed to prepare N-phenylmaleimide by this method, using acetic anhydride as the dehydrating agent and working in the presence of sodium acetate.

It is also known (see U.S. Pat. Nos. 3,018,290 and 3,018,292) to carry out the cyclising dehydration of maleamic acids with a carboxylic acid anhydride or chloride, in the presence of at least 2 mols of tertiary amine per mol of maleamic acid.

For the preparation of N,N'-meta-phenylene-bis-maleimide, it has also been proposed (see U.S. Pat. 3,127,414) to react the corresponding bis-maleamic acid with acetic anhydride in the presence of sodium acetate in a polar organic solvent.

A process is also known (see French Pat. No. 2,055,969) for the preparation of N-substituted maleimides by reacting the corresponding maleamic acids with a lower carboxylic acid anhydride, in the presence of a tertiary amine, an organic diluent and a catalyst, the catalyst being a nickel derivative which is soluble in the liquid phase of the reaction mixture, from 0.1 to 0.5 mol of tertiary amine being used per molar group of the formula:

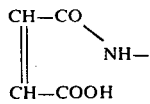 (I)

A continuous process has now been found for the preparation of N-substituted maleimides. This process comprises a. reacting in a first vessel, maleic anhydride and a primary amine in a medium which is a solvent for these reagents, under a pressure from 1 to 5 bars and at a temperature from 40° to 130°C, b. circulating the mixture thus produced through a closed circuit equipped with a condenser, while introducing a dehydrating agent, a tertiary amine and a catalyst into said circuit, c. continuously removing a portion of the reaction mixture which is circulating in the closed circuit, and d. isolating the maleimide from the mixture thus removed.

According to a particular embodiment of this process, the reaction mixture removed from the closed circuit is passed through one or more heating zones and then cooled before the maleimide is isolated.

In a typical process, maleic anhydride is dissolved in an anhydrous organic solvent to form a solution in which the concentration of anhydride is suitably between 20 and 30% by weight. Amongst the organic solvents which can be used, those which have a boiling point from 40°C to 130°C are particularly suitable. Amongst them, the following may be mentioned especially: hydrocarbons such as benzene, toluene and cyclohexane, chlorinated derivatives such as chlorobenzene and methylene chloride, cyclic and acyclic ethers such as tetrahydrofurane, dioxane or ethyl ether, and dialkyl ketones such as acetone and methyl ethyl ketone.

The solvent for the primary amine can be the same as that used for dissolving the anhydride or optionally another solvent which is miscible with the first. The concentration of the amine solution should generally be from 25 to 35% by weight.

Suitable primary amines which can be used include methylamine, aniline, ethylene-diamine, hexamethylenediamine, meta-phenylene-diamine, para-phenylene-diamine, benzidine, diaminodiphenylmethanes, diaminodiphenyl ethers, diaminodiphenylsulphones, diaminodicyclohexylmethanes, diaminodimethylene-cyclo-hexanes, diamino-meta-xylylenes, diamino-para-xylylenes, diaminodiphenylcyclohexanes, diaminodiphenylpropanes, diaminotriphenylethanes, diaminotriphenylmethanes and diaminotriazoles.

As the dehydrating agent, a carboxylic acid anhydride such as acetic anhydride is advantageously used in an amount at least equal to one mol per group of the formula (I) present in the maleamic acid prepared. Larger amounts, of the order of 1.05 to 1.2 mols per mol of acid, corresponding to 2.1 to 2.4 mols per mol of bis-maleamic acid, are generally used.

The dehydration reaction is preferably carried out in the presence of a tertiary amine. Amongst the suitable tertiary amines, trialkylamines and N,N-dialkylanilines in which the alkyl radicals have 1 to 12 carbon atoms may be mentioned. It is advantageous to use triethylamine and N,N-dimethylaniline. The preferred amounts of tertiary amine are from 0.15 to 0.4 mol per mol of mono-maleamic acid, that is to say from 0.3 to 0.8 mol per mol of bis-maleamic acid.

Suitable catalysts include nickel salts of carboxylic acids, especially nickel acetate tetrahydrate and nickel acetyl-acetonate. They are employed in very small amounts, generally of the order of 0.5 to 5 m.mols. per mol of maleamic acid, corresponding to 1 to 10 m.mols per mol of bis-maleamic acid.

The apparatus in which the reaction of maleic anhydride with the primary amine leading to the maleamic acid takes place should be a reactor which resists pressures of about 5 bars, the walls of which are equipped with baffles, and in which a stirrer equipped with blades rotates, making vigorous stirring possible. Solutions of the reagents are appropriately injected at the base of this apparatus. The dispersion thus produced is then driven through a closed circuit which passes through the upper part of this first apparatus. A closed circuit is in itself known for carrying out various operations including polymerisation (see AICHE Jal 15, T. T. Szabo and E. B. Nauman No. 4, p. 575 – 1969) and for mixing solutions (see "Chemical Engineering", COULSON- RICHARDSON p. 65). This closed circuit can in fact be any shape, but is preferably rounded, surmounted by a cyclone pot which makes it possible to check the pressure and to work under the pressure of an inert gas such as nitrogen. Branching ducts connected to this closed circuit make it possible to inject the reagents and to remove a portion of the mixture which circulates.

Since the reaction of maleic anhydride with the primary amine is exothermic and takes place in a closed system, an autogenic pressure is established which is from 1 to 5 bars (gauge), the temperature itself being from 40° to 130°C.

The quantity of mixture removed from the closed circuit is obviously similar or equal, by weight, to the quantity of the solutions of maleic anhydride and primary amine which is introduced into the first vessel.

The reaction started in this closed circuit can optionally continue in one or more apparatuses in series. The maleimide obtained is then cooled and thereafter precipitated, for example by adding distilled water to the solution in acetone, and is then filtered off.

The continuous process according to the invention possesses numerous advantages, such as:

short dwell time of the reagents in the equipment (approximately 3 hours), release of pressure from the suspension of maleamic acid without clogging, removal of the heat produced by the reaction leading to the maleamic acid, and direct and rapid solubilisation to this suspension in the cyclodehydration reaction mixture.

This process is particularly suitable for the preparation of N-substituted-bis-maleimides.

The following Example further illustrates the present invention.

EXAMPLE

The reaction is carried out in an apparatus which is illustrated diagrammatically in the Figure of the accompanying drawing in which: a metal cylinder (3), closed at both ends, of diameter 3.5 cm and height 20 cm (giving a volume of 116 cm$^3$), equipped internally with baffles and a stirrer equipped with blades, is provided, at the base, with two inlets, (1) and (2) which are connected to metering pumps, the upper part of the said cylinder forming part of a closed circuit reactor (4). The reactor (4) consist of a stainless steel tube of internal diameter 1.4 cm, connected to the cylinder (3) as stated above, and comprising, in order, a circulating pump, an outlet tube connected to a pressure release valve (10), three inlet tubes, (6) (7) and (8), a condenser (9) and a stainless steel cyclone pot (5) of diameter 5.6 cm and height 80 cm (giving a useful volume of 2.98 liters), located at the upper part of the circuit and possessing a calibrated safety valve. A row of three glass flasks (11), each of 8 liters, connected in series, each of which is equipped with a central stirrer, a heating device and a condenser (12) drawing on a nitrogen reservoir, is provided, the first flask of the series being connected to the pressure release valve (10) and the last to a condenser (13) which is itself connected downstream to a 10 liter stainless steel crystallising vessel (14) equipped with a central stirrer.

A solution of 1,000 g of maleic anhydride in 2,900 g of acetone (flow rate 4.4 l/hour), and a solution of 990 g of 4,4'-diamino-diphenylmethane in 2,446 g of acetone (flow rate 4.150 l/hour) are conveyed respectively via the tubes (1) and (2), continuously and be means of metering pumps, into the cylinder (3).

The rate at which the stirrer rotates is adjusted to 700 revolutions/minute. Under normal working conditions, the temperature in the apparatus rises to 65°C and the pressure rises to 2.2 bars. Under these working conditions, the dwell time of the reagents in the cylinder is 1 minute. The very viscous suspension of bis-maleamic acid formed in the cylinder is then driven into the closed circuit reactor. 1,275 g of acetic anhydride, 240 g of triethylamine and 96 g of a solution of nickel acetate consisting of 86 g of water and 10 g of nickel acetate are injected simultaneously and continuously into the closed circuit reactor, via the side inlet tubes (6), (7) and (8). For the period during which the process is being carried out, the circulating pump situated in the lower part of the closed circuit reactor pumps at the rate of 1,300 l/hour, thus introducing turbulent conditions (25 × 10$^3$ Reynolds measured at the upper part of the reactor). Under normal working conditions, the temperature in the closed circuit reactor is 63°C and the pressure is 2.2 bars. The cyclone pot is connected to a nitrogen reservoir under a pressure of 2.2 bars.

The product from the reactor is removed continuously via the side valve (10) at the rate of 20 l/hour, which represents an average dwell time of the reagents of about 18 minutes. The cyclodehydration is completed in the glass flasks in which the mixture is kept under reflux (63°C). The average dwell time of the mixture in each flask is about 48 minutes. After having passed through all the flasks, the reaction product is cooled to 25°C by passing it through the condenser (13) and it is then conveyed to the crystallising vessel (14) where distilled water at 20°–25°C is added continuously at the rate of 27 l/hour. The bis-maleimide precipitates instantaneously and the supernatant liquid is then conveyed to a filter.

After 3 hours 30 minutes, 1,673 g of a product are thus produced, the chemical analysis of which shows that it contains 75% by weight of N,N'-4,4'-diphenylmethane-bis-maleimide.

I claim:

1. In a process for the preparation of an N-substituted maleimide which comprises preparing the corresponding maleamic acid from maleic anhydride and a primary amine and reacting said acid with a carboxylic acid anhydride and a tertiary amine selected from a trialkylamine and an N,N-dialkylaniline, in which the alkyl radicals have 1 to 12 carbon atoms in the presence of a nickel catalyst, the improvement which comprises carrying out the process continuously by:
   a. reacting in a first vessel, maleic anhydride and a primary amine in a solvent for the anhydride and amine, under a pressure from about 1 to 5 bars and at a temperature from about 40° to 130°C.,
   b. circulating the mixture thus produced through a closed circuit equipped with a condenser, while introducing the carboxylic acid anhydride, tertiary amine and catalyst into said circuit,
   c. continuously removing part of the reaction mixture which is circulating in the circuit, and
   d. isolating the maleimide from the mixture thus removed.

2. Process according to claim 1, in which the reaction mixture removed in (c) in passed through one or more heating zones and then cooled before the maleimide is isolated.

3. Process according to claim 1, in which the primary amine is 4,4'-diamino-diphenylmethane.

4. Process according to claim 1, in which the solvent used in (a) has a boiling point from 40° to 130°C.

5. Process according to claim 4, in which the solvent is acetone.

6. Process according to claim 1, in which the carboxylic acid anhydride is acetic anhydride.

7. Process according to claim 1, in which the tertiary amine is triethylamine.

8. Process according to claim 1, in which the catalyst is a nickel derivative which is soluble in the liquid phase of the reaction mixture.

9. Process according to claim 8, in which the catalyst is nickel acetate tetrahydrate or nickel acetylacetonate.

10. Process according to claim 1 in which from 0.1 to 0.5 mol of tertiary amine are used per molar group of the formula:

$$\begin{array}{c} \text{CH—CO} \\ \| \quad\quad\quad \diagdown \\ \quad\quad\quad\quad \text{NH—} \\ \text{CH—COOH} \end{array}$$

11. Process according to claim 1 in which from 1.05 to 1.2 mols of carboxylic acid anhydride and from 0.15 to 0.4 mol of tertiary amine are used per molar group of the formula:

$$\begin{array}{c} \text{CH—CO} \\ \| \quad\quad\quad \diagdown \\ \quad\quad\quad\quad \text{NH—} \\ \text{CH—COOH} \end{array}$$

* * * * *

UNITED STATES PATENT OFFICE
CERTIFICATE OF CORRECTION

Patent No. 3,960,887              Dated June 1, 1976

Inventor(s)  Pierre RENARD

It is certified that error appears in the above-identified patent and that said Letters Patent are hereby corrected as shown below:

Line [73] name of Assignee should be changed from "Rhone-Poulene" to --Rhone-Poulenc S.A.--

Signed and Sealed this

Twenty-eighth Day of December 1976

[SEAL]

Attest:

RUTH C. MASON
*Attesting Officer*

C. MARSHALL DANN
*Commissioner of Patents and Trademarks*